(12) United States Patent
Langeland et al.

(10) Patent No.: US 9,924,922 B2
(45) Date of Patent: Mar. 27, 2018

(54) GRAPHICAL DISPLAY OF CONTRACTIBLE CHAMBER

(71) Applicant: General Electric Company, Schenectady, NY (US)

(72) Inventors: Stian Langeland, Horten (NO); Sten Roar Snare, Olso (NO)

(73) Assignee: General Electric Company, Schenectady, NY (US)

( * ) Notice: Subject to any disclaimer, the term of this patent is extended or adjusted under 35 U.S.C. 154(b) by 569 days.

(21) Appl. No.: 14/596,792

(22) Filed: Jan. 14, 2015

(65) Prior Publication Data
US 2016/0199032 A1 Jul. 14, 2016

(51) Int. Cl.
*A61B 8/00* (2006.01)
*A61B 8/08* (2006.01)

(52) U.S. Cl.
CPC .......... *A61B 8/0883* (2013.01); *A61B 8/0891* (2013.01)

(58) Field of Classification Search
CPC ............................ A61B 8/0883; A61B 8/0891
USPC ................................................. 600/437–469
See application file for complete search history.

(56) References Cited

U.S. PATENT DOCUMENTS

| | | | |
|---|---|---|---|
| 2007/0038061 A1* | 2/2007 | Huennekens | A61B 6/504 600/407 |
| 2009/0082668 A1* | 3/2009 | Hamada | A61B 8/483 600/443 |
| 2011/0033098 A1* | 2/2011 | Richter | G06T 7/12 382/131 |
| 2012/0172698 A1* | 7/2012 | Teo | A61B 5/0066 600/407 |
| 2013/0109958 A1* | 5/2013 | Baumgart | A61B 8/12 600/424 |
| 2014/0275996 A1* | 9/2014 | Stigall | A61B 6/5247 600/424 |

\* cited by examiner

*Primary Examiner* — Sanjay Cattungal

(57) ABSTRACT

Disclosed is a process for displaying ultrasound data representative of a rotationally symmetrical contractible chamber or vessel within a patient which involves obtaining ultrasound data from the ultrasound imaging of the vessel or chamber through at least a phase of one cardiac cycle and virtually sectioning the vessel or chamber into multiple circumferential segments, each extending its own longitudinal distance from a common reference point. The data is used to obtain rotational parameters representative of an entire circumferential segment of the chamber or vessel. The process is repeated until a rotational parameter for each entire circumferential segment along a desired distance of the longitudinal axis of the chamber or vessel has been obtained. The rotational parameters are displayed in a two dimensional format having annular rings with each annular ring being representative of a given circumferential segment.

18 Claims, 3 Drawing Sheets

GRAPHICAL DISPLAY OF CONTRACTIBLE CHAMBER

BACKGROUND

Certain chambers of the heart and arteries contract and relax in accordance with the cardiac cycle. This contraction and relaxation causes some rotation of the involved tissue. Left ventricular rotation may be used as clinical markers of myocardial function.

SUMMARY

A process for displaying ultrasound data representative of a rotationally symmetrical contractible chamber or vessel within a patient involves obtaining ultrasound data from the ultrasound imaging of the vessel or chamber through at least a phase of one cardiac cycle and virtually sectioning the vessel or chamber into multiple circumferential segments, each extending its own longitudinal distance from a common reference point. The data is used to obtain rotational parameters representative of an entire circumferential segment of the chamber or vessel. The process is repeated until a rotational parameter for each entire circumferential segment along a desired distance of the longitudinal axis of the chamber or vessel has been obtained. The rotational parameters are displayed in a two dimensional format having annular rings with each annular ring being representative of a given circumferential segment.

An apparatus for displaying ultrasound data representative of a chamber of the human heart involves a processor that receives ultrasound data from the ultrasound imaging of the left ventricle of a human heart through a phase of a cardiac cycle and operates on the data by virtually sectioning the ventricle into multiple circumferential segments. It then obtains rotational parameters representative of an entire circumferential segment of the ventricle centered at a given height above the apex of the heart and repeats the process until a rotational parameter for each entire circumferential segment between the base and the apex has been obtained and causes the rotational parameters to a display in a two dimensional format having annular rings with each annular ring being representative of a given segment. The apparatus also includes a display device which displays the rotational parameters in this two dimensional format.

DETAILED DESCRIPTION

The chambers of a live heart contract and relax with the cardiac cycle. This contraction and relaxation causes some rotation and/or twisting of the tissue that defines the heart chamber. The twisting or rotational parameters of the tissue defining the chamber can be derived from ultrasound data. The rotational parameters are used to identify diseased regions of the heart. In one embodiment, as discussed below the rotational parameters are displayed in a manner to identify the diseased areas of the heart.

The functioning of a live heart is monitored by taking an ultrasound image of the heart or select portions of the heart as it passes through one or more cardiac cycles. It is convenient to take an ultrasound image of just a given portion of the heart in a given cardiac cycle and to take ultrasound images of other portions over successive cardiac cycles until a composite image of the entire heart or a chamber of interest, such as the left ventricle, is built up. This may be accomplished by directing the ultrasound beam to a given portion in each cardiac cycle. The ultrasound data used to create this complete image can then be probed to tease out various rotational parameters. These parameters can be developed for circumferential segments of the chamber being examined. Then the rotational parameter of interest can be displayed in a two dimensional format with each circumferential segment being assigned an annulus to yield a display colloquially referred to as a bull's eye or target format. In one embodiment the target format includes a plurality of concentric rings of differing diameters. The region defined by the concentric ring of smallest diameter is often referred to as the bull's eye. Other portions of the circulatory system, which undergo rotational change through the course of a cardiac cycle and have rotational symmetry, can be examined using the same technique.

Figure 1:
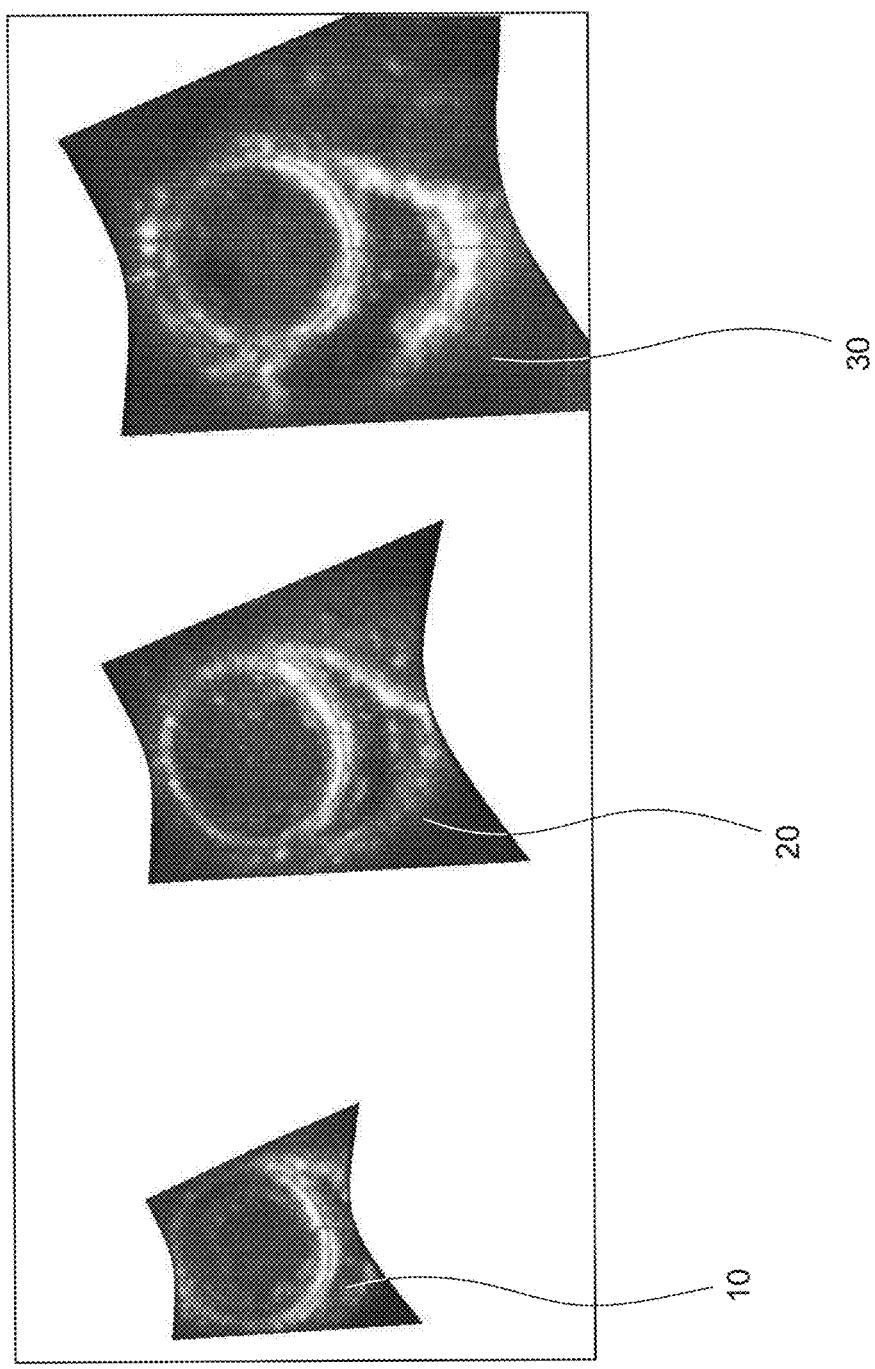
FIG. 1 is a set of ultrasound images of the left ventricle of a human heart taken along planes perpendicular to the long axis of the ventricle.

Referring to FIG. 1, the left ventricle of a human heart has been virtually sectioned into three circumferential segments by planes. Each plane is perpendicular to a longitudinal axis of the left ventricle. Ultrasound images 10, 20 and 30 have been provided that are representative of each circumferential image proceeding upward from the apex of the heart. Stated another way, ultrasound images 10, 20 and 30 represent cross-sectional segments of the left ventricle of a human heart. The cross sectional segment 10 represented in ultrasound image 10 corresponds to an apex region of the left ventricle. The cross sectional segment 20 corresponds to a center region of the left ventricle. Finally, cross sectional segment 30 corresponds to the region of the left ventricle distal to the apex. Since each ultrasound image is a cross sectional segment of a particular plane of the left ventricle results in an image of the circumferential wall of the left ventricle. Accordingly, images 10, 20 and 30 will be referred to herein as circumferential segments.

Figure 2:
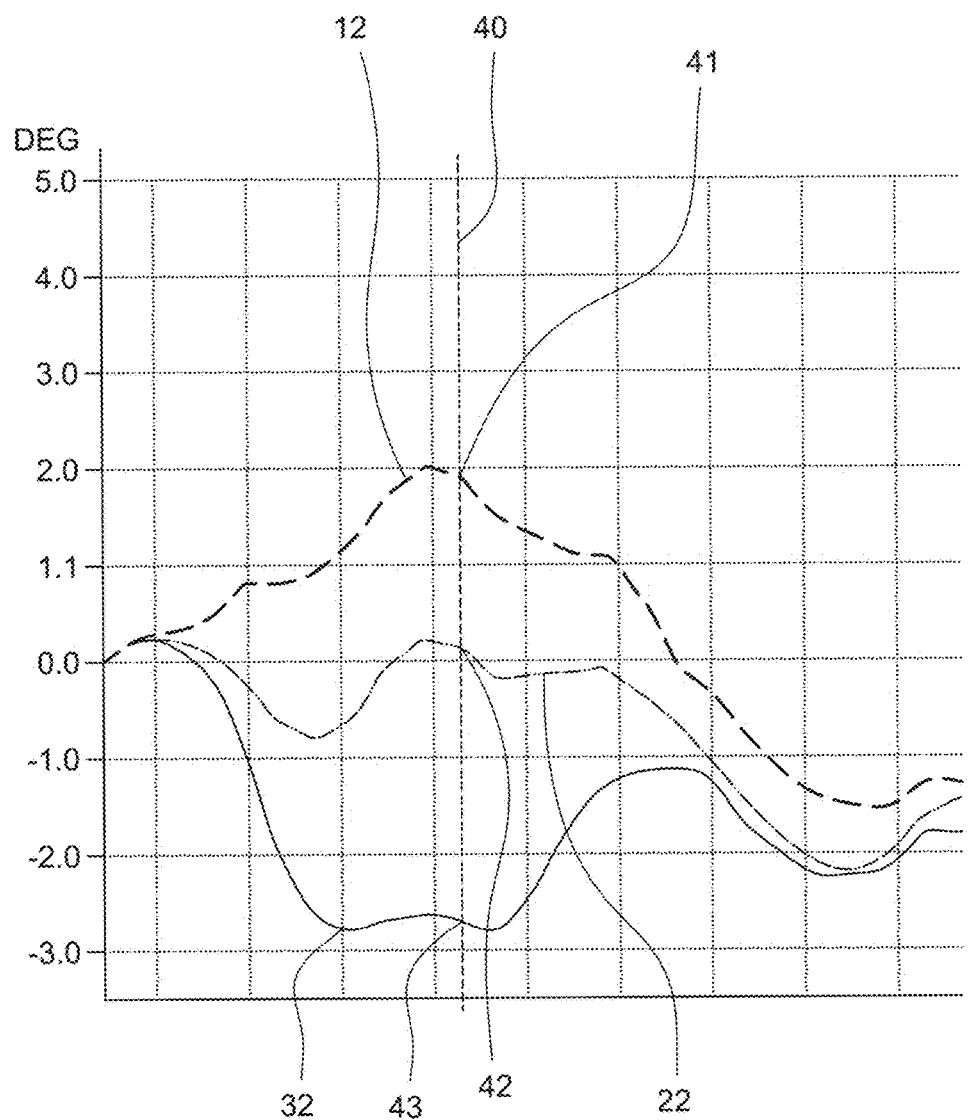
FIG. 2 is a set of graphs for three circumferential segments of the left ventricle of the rotation in degrees versus the time position in seconds in a cardiac cycle.

Referring to FIG. 2, the rotation of each segment has been plotted against a temporal point in the cardiac cycle of the human heart that is virtually sectioned in FIG. 1. FIG. 2 is a graph having a y-axis defining the degree of rotation of a portion of the left ventricle and having an x-axis defining time into a cardiac cycle. The amount of rotation is determined by comparing the location of a portion of the left ventricle at the beginning of the cardiac cycle and a point of time during the cardiac cycle.

The rotation of each circumferential segment is plotted against the time into the cardiac cycle. In one embodiment, the rotation of a circumferential segment is determined by averaging the rotation of a series of points about the circumferential segment. The average value or rotation of the circumferential segment is then plotted on the graph in FIG. 2. It is also contemplated that the rotational value for each circumferential segment may be calculated by a different algorithm. Referring to FIG. 2. the rotation of the circumferential segment 10 has as rotational value of 1.8 degrees at time point 40. Similarly, the rotation of the circumferential segment 20 has a rotational value of 0.1 degree at time point 40; and the rotation of the circumferential segment 30 has a rotational value of −2.7 degrees at time point 40.

For each circumferential segment, the rotational value is determined at different times throughout the cardiac cycle. Line 40 represents a particular point in the cardiac cycle. The value of the rotation parameter for each of the circumferential segments 10, 20 and 30 at the point represented by line 40 is determined by the intersections 41, 42 and 43, respectively. So, for instance, the rotation of circumferential segment 10 at the temporal point represented by line 40 may be determined from the intersection 41 of line 40 with curve 12. The values in degrees for intersections 41, 42 and 43 are 1.8, 0.1 and −2.7, respectively.

Lines 12, 22 and 32 represent the rotational values of the circumferential segments 10, 20 and 30 respectively throughout the cardiac cycle. Accordingly a plurality of sets of ultrasound data representative of each circumferential segment are obtained throughout the cardiac cycle to create the data required for the lines 12, 22 and 32 in FIG. 2.

Figure 3:
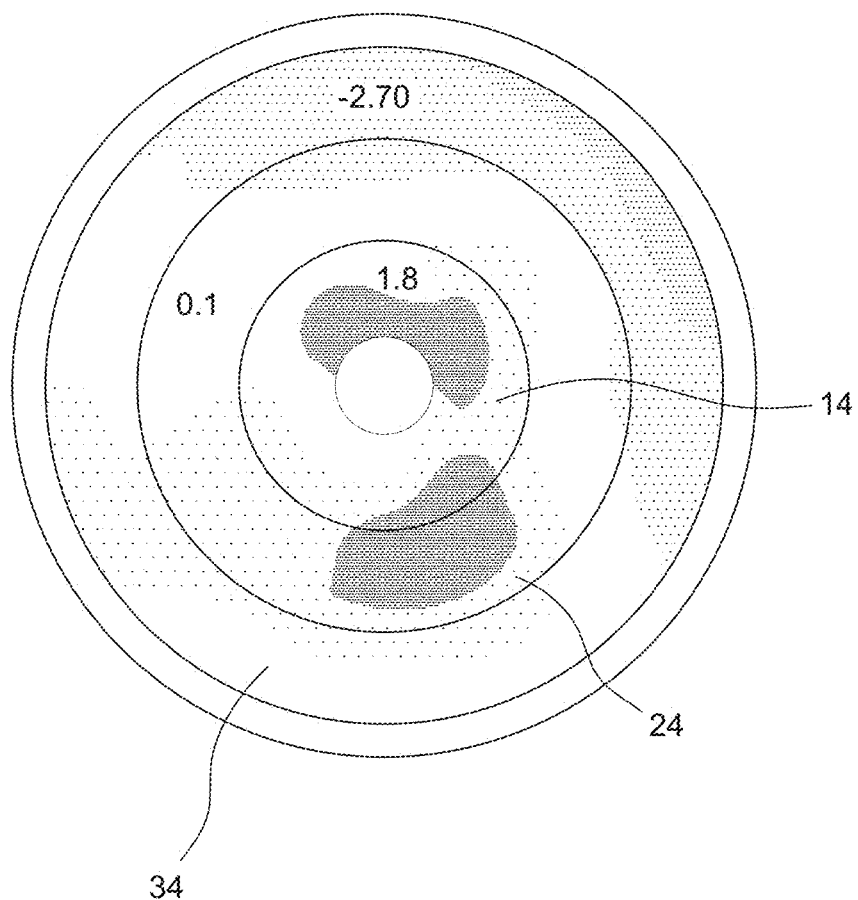
FIG. 3 is a graphical display in a target or bull's eye format of the degree of rotation for a particular time point for three circumferential segments of the left ventricle.

Referring to FIG. 3, the degree of rotation data for each of the circumferential segments is shown in a bull's eye format with each circumferential segment being assigned its own ring. Thus the 1.8° rotation for circumferential segment 10 is shown in ring 14, the 0.1° rotation for circumferential segment 20 is shown in ring 24 and the −2.7° rotation for circumferential segment 30 is shown in ring 34.

In one embodiment more than three circumferential segments are obtained. In one embodiment 15 circumferential segments are obtained though it is contemplated that there may be more than or fewer than 15 circumferential segments. The 15 circumferential segments are taken such that they are evenly spaced from one another along the longitudinal axis of the left ventricle. It is also contemplated that the circumferential segments may be obtained such that they are not evenly spaced from one another if a particular area of the left ventricle or chamber being analyzed is of interest. Referring to FIG. 3 the region between the innermost circle and next outwardly radial circle encompasses in one example five circumferential segments. The shading represents a scale between a positive rotation and a negative rotation. In one embodiment the shading is a color scale. In one embodiment 24 rotational parameters are calculated for each circumferential segment and are illustrated on FIG. 3 as a shade or color representing the value of rotation. In one embodiment the space between the circumferential segments in each region is extrapolated to provide continuous shading on the bull's eye image. In one embodiment each data point is illustrated by a dot or region of shading or color. The rotational values of all of the data points of the circumferential segments are then averaged and provided as a value on the bull's eye format. In one example where five circumferential segments make up each region and 24 data points are obtained for each circumferential ring, the 1.8 degree rotation represents the average of all 120 data points. Similarly, an additional five circumferential segments make up the region between the second circle and the next larger circle on the bull's eye format of FIG. 3. The value of 0.1 degrees represents the average rotational value of all 120 data points obtained for this second region. Finally, the third region represented by the third outer ring and fourth outer ring value of −2.7 degrees represents the average of the 120 data points taken in this third region.

In one embodiment the rotational values of each region is represented by a single number where that value is not the average but a value derived from another algorithm.

The same data treatment can be applied to other rotational parameters such as torsion, torsion rate or velocity. It may be convenient to display the maximum value of the rotational parameter being treated. The instantaneous velocities of circumferential segments could be conveniently rendered as rings in a bull's eye display, provided that adequate temporal resolution can be obtained. It may be convenient to use colors to be representative of one or more of the rotational parameters displayed in the bull's eye format.

One approach is to gather ultrasound data from different portions of each circumferential segment in each of multiple cardiac cycles and combine the data to yield a rotational parameter value representative of an entire circumferential segment. Thus it may take multiple cardiac cycles, for instance six, to derive a value of a rotational parameter representative of an entire circumferential segment. Relying on the reasonable assumption that each cardiac cycle will be essentially a repeat of the previous one, if nothing is done to perturb the patient, the data acquisition and processing data processing capacity can be efficiently focused. The ultrasound data from a particular portion of a chamber that represents only a part of a given circumferential segment can be obtained from a particular portion of a given cardiac cycle, say the contraction phase. Then ultrasound data from other portions of that circumferential segment can be obtained from the same portion of succeeding cardiac cycles.

The data used to populate the graphs and rings, such as graphs 12, 22 and 32 and rings 14, 24 and 34, need not be drawn from a single cardiac cycle, Rather values from the same point in time of the cardiac cycle over several cardiac cycles, for instance from six cycles, may be averaged.

Each of the rings in a given bull's eye display need not be representative of the same temporal point in a cardiac cycle as the other rings. It may be convenient for each of the rings to be representative of the maximum value of a given rotational parameter observed for its circumferential segment over a cardiac cycle. So adjacent rings in such a display may be representative of values of a rotational parameter at different temporal points in a cardiac cycle. For instance, the user may have reason to track the maximum for a given rotational parameter in each circumferential segment and be able to view these maxima in a single display. This parameter may reach its maximum value for each circumferential segment at a different temporal point in the cardiac cycle. Thus each ring in the display will be representative of the parameter maximum but have a different temporal place in the cardiac cycle from the other rings.

It may be convenient to obtain the ultrasound data that is processed to the display from the contraction phase of the cardiac cycle. The phase that is examined can be left for selection by the user. For instance a cardiologist may have reason to focus on a different phase of the cycle, such as the relaxation phase. This selection may be driven by the parameter that is being derived from the data or the physiological condition that is being studied. The power or benefit of the bull's eye display with unitary annular rings is not limited to any particular phase of the cardiac cycle.

It may be convenient to follow a particular rotational parameter through an entire cardiac cycle or a portion thereof, rather than just observing it in the bull's eye display with unitary annular rings for a given temporal point. The processor can be conveniently programmed to present a series of such displays representative of different temporal points along a cardiac cycle. For instance, referring to FIG. 2 a bull's eye display could be generated for each of a variety temporal points as opposed to just the one represented by line 40 to yield a series of displays similar to that of FIG. 3.

The rotational parameter subjected to the present bull's eye display treatment may be one that has a value at a fixed temporal point in the cardiac cycle such as the degree of rotation or the torsion. Or it may be one that has a derived value at a fixed temporal point in the cardiac cycle such as the torsion rate or the instantaneous velocity. In the latter case data must be gathered from either before or after the temporal point or both. Nonetheless the derived values can be treated in the same way as the direct values of the other parameters to give a representative display.

A significant benefit of this data display approach is that it gives a representative overview of the parameter being examined while avoiding the creation of distracting artifacts that could arise if the ultrasound data were processed to create a parameter for rotational portions of each circumferential segment. Thus an advantage is obtained in cumulating the ultrasound data for conversion into a parameter at the optimum level of generality. Too general a view, for instance accumulation over an entire symmetrical chamber, such as the left ventricle of the human heart, may fail to give the desired information with regard to particular portions. For instance, there may be a desire to identify diseased or damaged tissue or assess the degree or extent of the disease or damage. On the other hand, too fine accumulation may create artifacts that are not truly representative of the diseased or damaged tissue. For instance, the rotational performance of healthy tissue immediately adjacent to diseased or damaged tissue may be effected by its proximity to such tissue and too fine a data treatment will display this proximity effect creating an artifact.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A process for displaying ultrasound data representative of a contractible chamber or vessel within a patient;
    obtaining ultrasound data from the ultrasound imaging of the vessel or chamber through at least a phase of one cardiac cycle;
    virtually sectioning the vessel or chamber into multiple circumferential segments, each extending its own longitudinal distance from a common reference point;
    obtaining a plurality of rotational parameters, where each of the plurality of rotational parameters is obtained from a different one of the multiple circumferential segments; and
    displaying the rotational parameters in a bull's eye format comprising a plurality of concentric rings of differing diameters, where each of the plurality of concentric rings represents the rotational parameter of a different one of the multiple circumferential segments.

2. The process of claim 1 wherein the ultrasound data is representative of a chamber of the heart that is one of the atrium and the left ventricle of a heart.

3. The process of claim 2 wherein the heart chamber is sectioned into four virtual circumferential segments.

4. The process of claim 2 wherein the heart chamber is the left ventricle.

5. The process of claim 4 wherein no numerical data is displayed for the virtual circumferential segment that encompasses the apex of the heart.

6. The process of claim 1 wherein the displayed data includes the maximum torsion to which a virtual circumferential segment has been subjected in a phase of a cardiac cycle of the heart.

7. The process of claim 1 wherein the displayed data includes the maximum torsion rate to which a virtual circumferential segment has been subjected in a phase of a cardiac cycle of the heart.

8. The process of claim 1 wherein the displayed data includes the maximum rotation to which a virtual circumferential segment has been subjected in a phase of a cardiac cycle of the heart.

9. The process of claim 1 wherein the phase of the cardiac cycle for which ultrasound data is obtained is the contraction phase.

10. The process of claim 1 wherein the displayed data includes the maximum instantaneous velocity for a given point in the heart cycle to which a virtual circumferential segment has been subjected in a phase of a cardiac cycle of the heart.

11. The process of claim 1 wherein the ultrasound data is taken over multiple cardiac cycles.

12. The process of claim 10 wherein each of the plurality of rotational parameters is an average value over the cardiac cycles for which ultrasound data is obtained.

13. The process of claim 1 wherein various colors are used to represent different rotational parameters displayed in the bull's eye format.

14. An apparatus for displaying ultrasound data representative of a chamber of the human heart comprising;
    a processor which receives ultrasound data from the ultrasound imaging of the left ventricle of a human heart through a phase of a cardiac cycle and operates on the data by:
        virtually sectioning the ventricle into multiple circumferential segments;
        obtaining rotational parameters representative of an entire circumferential segment of the ventricle centered at a given height above the apex of the heart,
        repeating the process until a rotational parameter for each entire circumferential segment between the base and the apex has been obtained; and
        causing the rotational parameters to display in a bull's eye format comprising a plurality of concentric rings of differing diameters, where each of the plurality of concentric rings represents the rotational parameter of a different one of the multiple circumferential segments; and
    a display device which displays the rotational parameters in the bull's eye format.

15. The apparatus of claim 14 wherein the ultrasound data received by the processor is obtained from more than one cardiac cycle.

16. The apparatus of claim 14 wherein the processor obtains the rotational parameters by averaging the data from more than one cardiac cycle.

17. The apparatus of claim 14 wherein the processor also causes the display of various colors representative of one or more rotational parameters.

18. The apparatus of claim 14, wherein the ventricle is the left ventricle.

* * * * *